(12) United States Patent
Rousseau et al.

(10) Patent No.: US 8,911,466 B2
(45) Date of Patent: Dec. 16, 2014

(54) MEDICAL INSERTION DEVICE AND METHOD OF USE

(75) Inventors: Robert A. Rousseau, Ottsville, PA (US); David C. Lindh, Sr., Flemington, NJ (US)

(73) Assignee: Ethicon, Inc., Somerville, NJ (US)

( * ) Notice: Subject to any disclaimer, the term of this patent is extended or adjusted under 35 U.S.C. 154(b) by 377 days.

(21) Appl. No.: 13/309,751

(22) Filed: Dec. 2, 2011

(65) Prior Publication Data

US 2013/0139828 A1 Jun. 6, 2013

(51) Int. Cl.
*A61M 29/00* (2006.01)

(52) U.S. Cl.
USPC .............................. 606/191; 606/200; 128/848

(58) Field of Classification Search
CPC ............. A61B 2019/502; A61B 17/16; A61B 17/7098; A61B 2017/003; A61B 1/32; A61B 17/0483; A61B 17/0485; A61B 17/3423; A61B 2019/4836; A61B 2017/06185; A61B 2018/1407; A61B 17/3421; A61B 17/03
USPC ........... 128/848, 859–862; 602/902; 606/110, 606/113, 114, 200, 191
See application file for complete search history.

(56) References Cited

U.S. PATENT DOCUMENTS

| 6,517,550 | B1 * | 2/2003 | Konya et al. ................. 606/113 |
| 7,367,340 | B2 | 5/2008 | Nelson et al. |
| 2008/0154286 | A1 | 6/2008 | Abbott et al. |
| 2008/0300607 | A1 | 12/2008 | Meade et al. |
| 2010/0010457 | A1 * | 1/2010 | Ewers et al. ................. 604/272 |
| 2012/0289998 | A1 * | 11/2012 | Fleming, III ................. 606/200 |

FOREIGN PATENT DOCUMENTS

| WO | 96/20649 A1 | 7/1996 |
| WO | 2008/057047 A1 | 5/2008 |
| WO | 2012/034131 A2 | 3/2012 |

* cited by examiner

*Primary Examiner* — Michael A. Brown
(74) *Attorney, Agent, or Firm* — Melissa J. Szanto

(57) ABSTRACT

An insertion device and method of use for treating obstructive sleep apnea. The device includes an outer tubular element with a tissue penetrating end and a side opening, an inner tubular element positioned partially within the outer member and movable longitudinally relative to it, a grasping device fixedly coupled to the inner element, and a central shaft extending through the inner tubular element and movable longitudinally relative to the inner and outer tubular elements. The central shaft is slidably coupled with the grasping device. The inner tubular element is further movable between a retracted position wherein the grasping device is positioned entirely within the outer tubular element, and an extended position wherein it extends outwardly therefrom through the side opening. In the extended position, the grasping device is adapted to grasp a filamentary element positioned external of the outer tubular element and in proximity thereto.

14 Claims, 20 Drawing Sheets

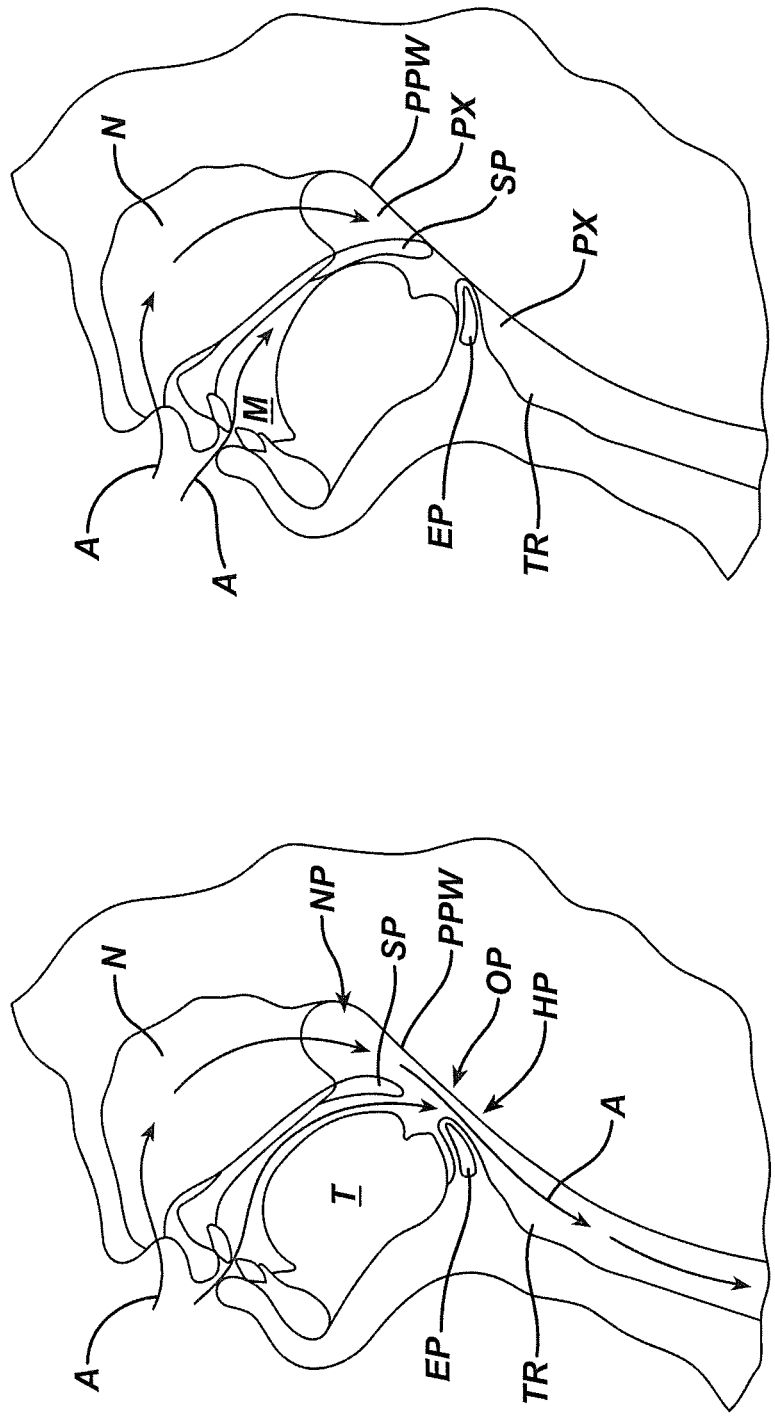

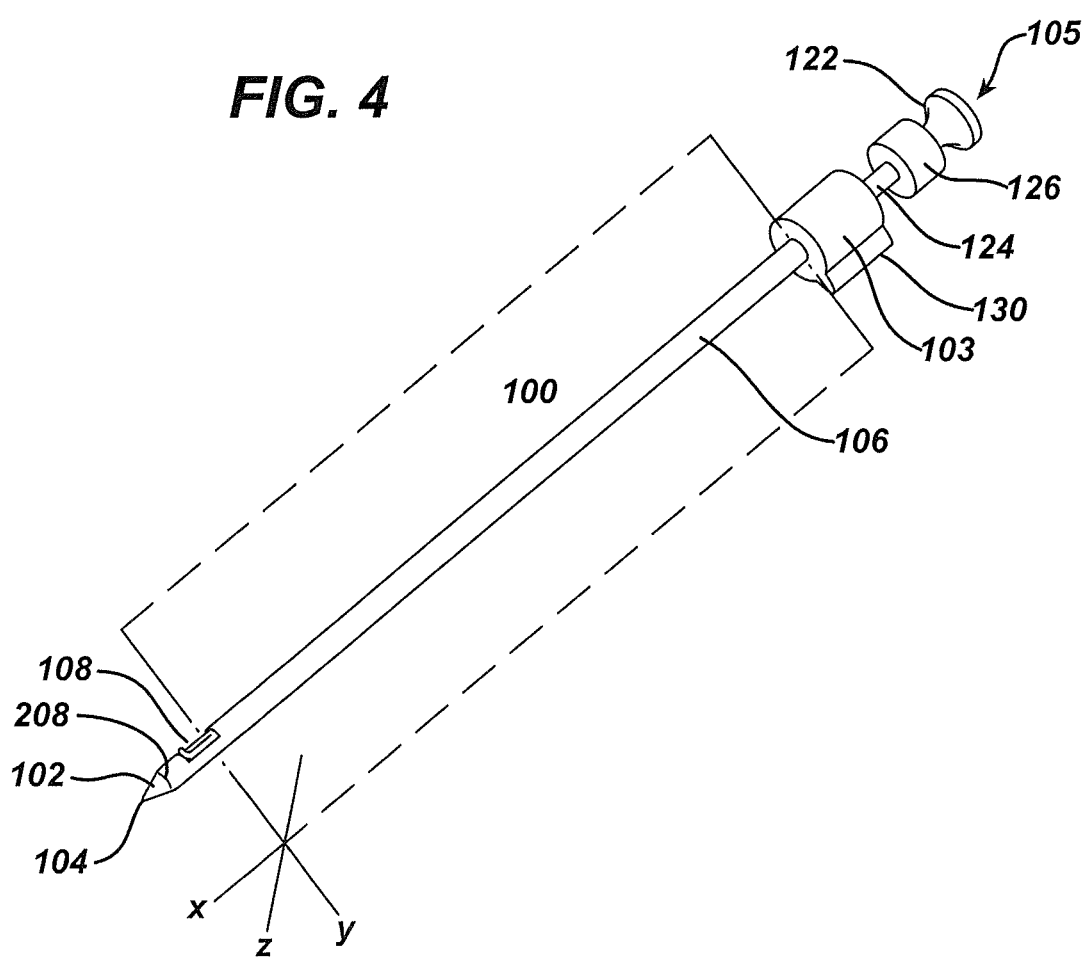

MEDICAL INSERTION DEVICE AND METHOD OF USE

FIELD OF THE INVENTION

The present invention relates generally to the field of medical devices, and more particularly to medical insertion devices having particular application for inserting implantable medical devices.

BACKGROUND

Obstructive sleep apnea (OSA) is a medical condition that is caused by a blockage of the airway, which usually occurs when the soft tissue in the throat collapses and closes during sleep. According to the National Institutes of Health, OSA affects more than twelve million Americans. During each apnea event, the brain briefly arouses the sufferer in order to initiate the resumption of breathing. This type of sleep, however, is extremely fragmented and of poor quality. When left untreated, OSA may result in high blood pressure, cardiovascular disease, weight gain, impotency, headaches, memory problems, job impairment, and motor vehicle crashes. Despite the seriousness of OSA, a general lack of awareness among the public and healthcare professionals results in the vast majority of OSA sufferers remaining undiagnosed and untreated.

In the human body, the air filled space between the nasal cavity and the larynx is referred to as the upper airway. The most critical part of the upper airway associated with sleep disorders is the pharynx. The pharynx has three different anatomical levels. The nasopharynx is the upper portion of the pharynx located in the back of the nasal cavity. The oropharynx is the intermediate portion of the pharynx containing the soft palate, the epiglottis, and the curve at the back of the tongue. The hypopharynx is the lower portion of the pharynx located below the soft tissue of the oropharynx. The oropharynx is the section of the pharynx that is most likely to collapse due to the high prevalence of soft tissue structure, which leaves less space for airflow. The hypopharynx lies below the aperture of the larynx and behind the larynx, and extends to the esophagus.

As is well known to those skilled in the art, the soft palate and the tongue are both flexible structures. The soft palate provides a barrier between the nasal cavity and the mouth. In many instances, the soft palate is longer than necessary and it extends a significant distance between the back of the tongue and the posterior pharyngeal wall.

Although the muscles relax throughout the body during sleep, most of the muscles of the respiratory system remain active. During inhalation, the diaphragm contracts and causes negative pressure to draw air into the nasal cavity and mouth. The air then flows past the pharynx, through the trachea and into the lungs. The negative pressure causes the tissue of the upper airway to deform slightly, which narrows the airway passage. In apneic patients, the soft palate, the tongue, and/or the epiglottis collapse against the posterior pharyngeal wall to block airflow into the trachea. As the airway narrows, airflow through the pharynx becomes turbulent which causes the soft palate to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep. If apnea or hypopnea occurs more than five times per hour, most medical personnel diagnose the individual as having an upper airway resistance problem. Many of these patients exhibit symptoms related to sleep disorders including sleepiness during the day, depression, and difficulty concentrating.

Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

When an individual is awake, the back of the tongue and the soft palate maintain their shape and tone due to their respective internal muscles. As a result, the airway through the pharynx remains open and unobstructed. During sleep, however, the muscle tone decreases and the posterior surface of the tongue and the soft palate become more flexible and distensible. Without normal muscle tone to keep their shape and to keep them in place either alone or as a group, the posterior surface of the tongue, the epiglottis, and the soft palate SP tend to easily collapse to block the airway.

One known treatment, commonly referred to as continuous positive airway pressure (CPAP), is currently the "gold standard" for treating OSA and operates by delivering air into a patient's airway through a specially designed nasal mask or pillow. The flow of air creates positive pressure when the patient inhales to keep the airway open. Although CPAP is considered by many to be an effective non-surgical treatment for the alleviation of snoring and obstructive sleep apnea, patients complain about discomfort caused by the mask and hoses, including bloating, nasal drying, and dry eyes. As a result, patient compliance for CPAP is only about 40%.

Surgical treatments have also been used to treat OSA. One such treatment is referred to as uvulopalatopharyngoplasty, which involves removing about 2 cm of the trailing edge of the soft palate to reduce the soft palate's ability to flutter between the tongue and the pharyngeal wall. Another procedure uses a surgical laser to create scar tissue on the surface of the soft palate, which reduces the flexibility of the soft palate for reducing snoring and/or closing of the air passage. Yet another procedure, commonly referred to as cautery-assisted palatal stiffening operation (CAPSO), is an office-based procedure performed under local anesthesia whereby a midline strip of soft palate mucosa is removed, and the wound is allowed to heal whereupon the flaccid palate is stiffened.

Surgical procedures such as those mentioned above continue to have problems. More specifically, the area of tissue that is surgically treated (i.e., removal of palatal tissue or scarring of palatal tissue) is often larger than is necessary to treat the patient's condition. In addition, the above-mentioned surgical procedures are often painful with extended, uncomfortable healing periods. For example, scar tissue on the soft palate may present a continuing irritant to the patient. Furthermore, the above procedures are not reversible in the event of adverse side effects.

Surgical implants have also been used to treat OSA. U.S. Pat. No. 7,367,340 describes the use of an element that is anchored to the mandible and is capable of applying force within the tongue to prevent the tongue from collapsing during sleep. In the embodiments described, the device consists of an element that is attached to the mandible though drilling of the mandible to provide a rigid point of fixation. The method of attachment produces essentially the same risk to the dental anatomy and nerve structures within the mandible.

An additional tongue suspension device utilizes a bone screw in the mandible, but has the advantage of being adjustable. The device utilizes a flexible shape memory anchor within the tongue that is shaped similar to a grappling hook to engage the tissue within the tongue base. It is placed through a small incision in the sub-mental region and the suture is attached to a spool-like component attached to the mandible. Two to four weeks after healing, a small incision is made under the chin and a screw is turned to tighten the suture, thus pulling the device forward. While the device provides a simplified installation technique from within the sterile space, the anchors suffered from a high rate of device fracture and failure due to loading within the tongue musculature. Additionally, the risk of damage to the teeth or the nerve roots for the teeth is similar in both devices.

Another implant system, sold under the name AIRvance by Medtronic, Inc. of Minneapolis, Minn., uses a titanium screw that is inserted into the posterior aspect of the mandible at the floor of the mouth. A loop of suture is passed through the tongue base and attached to the mandibular bone screw. The procedure achieves a suspension or hammock of the tongue base making it less likely for the base of the tongue to prolapse during sleep. Due to the high activity of the tongue during wakefulness, however, the suture component of this device may act as a cutting element within the tongue, causing device trans-location and ultimately a loss of efficacy of the procedure thereby requiring subsequent removal. Additionally, the fiber is placed within the tongue through the combination of a sterile and non-sterile approach. An incision is made within the sub-mental space to provide access to the infra-mandibular region to place the screw. Once the screw is attached to the mandible, the fiber element is passed into the tongue through the sub-mental musculature, through the genioglossus and exits out of the mucosal surface of the tongue into the contaminated oral cavity. This passage is accomplished through the use of a linear designed suture passer that grasps the fiber and forces it through the tongue in a straight path. Upon exiting in the oral cavity, the fiber is then passed laterally in a sub mucosal pass through the original puncture formed by the linear suture passer. The result of this type of passage is that the fiber is bent around a natural bend radius to fit within the puncture suture and remains sub mucosal during the healing phase. The open site is subject to contaminated fluid from the oral cavity upon seeping into the site and may potentially increase the likelihood of infection. This reliance upon the natural bend radius of the fiber can cause the tissue puncture site to be propped open by the fiber, particularly when the fiber diameter/thickness is large or if the fiber is very stiff, as is found with highly oriented high strength fibers. In order to avoid this propping mechanism, finer diameter/thickness fibers are utilized. This reduction in diameter limits the strength of fiber that may ultimately be utilized or limits the cross sectional area of the fiber that may be utilized which results in low load bearing surfaces within the tongue which may facilitate tissue pull through by the finer fiber.

For sake of clarity, FIG. 21a illustrates typical prior art placement of a tongue suspension loop 1 that is passed linearly from the sub-mental region, through the genioglossus 2 into the oral cavity and then laterally through the site of the single puncture 3. FIG. 21b illustrates the typical propping of the puncture site 3 as a result of the suture bend radius after tension is applied providing too large of a radius to allow the mucosa to close over the bent fiber.

In spite of the above advances in tongue suspension devices, there remains a need for a tongue suspension method and device that enables the use of larger diameter/cross sectional fibers to provide adequate load bearing surfaces and fiber tensile strengths.

SUMMARY OF THE INVENTION

The present invention provides an insertion device including an outer tubular element extending along a longitudinal axis and having a tissue penetrating distal end and a side opening therein positioned proximal of said tissue penetrating distal end; an inner tubular element extending along the longitudinal axis and positioned partially within an interior of the outer tubular member, and movable longitudinally relative to said outer tubular element; a grasping device fixedly coupled to the inner tubular element and extending outward in a distal direction from the inner tubular element; and a central shaft extending along the longitudinal axis and through an interior of the inner tubular element, and movable longitudinally relative to both the inner and outer tubular elements, a distal end of the central shaft being slidably coupled with the grasping device. The said inner tubular element is further movable between a retracted position wherein the grasping device is positioned entirely within the interior of the outer tubular element, and an extended position wherein the grasping device extends outwardly from the outer tubular element through the side opening. When the inner tubular element is in the extended position, the grasping device is movable between open and closed positions such that the grasping device is adapted to grasp a filamentary element positioned external of the outer tubular element and in proximity thereto.

In one embodiment, the grasper device further includes first and second grasping elements, and in yet another embodiment, the first and second grasping elements are opposing hook-like elements, which may be made of nitinol. In yet another embodiment, the first and second hook-like elements are opposing hooks have a twisted configuration relative to one another. In yet another alternative embodiment, the device further includes a visible indicator near the distal end of the outer tubular element.

Another embodiment further includes a first grasping element fixedly coupled to the outer tubular element such that movement of the first grasping element by a user causes movement of the outer tubular element longitudinally relative to the inner tubular element and central shaft; a second graspable element fixedly coupled to the inner tubular element such that movement of the second graspable element by a user causes movement of the inner tubular element longitudinally relative to the outer tubular element and central shaft; and a third graspable element fixedly coupled to the central shaft such that movement of the third graspable element by a user causes movement of the central shaft longitudinally relative to the inner and outer tubular elements.

According to yet another embodiment, the central shaft passes longitudinally through the inner tubular element via first and second openings in first and second closed ends of the inner tubular element respectively. The inner tubular element may optionally extend outwardly from an open proximal end of the outer tubular element.

Also provided is a kit for performing a surgical procedure for treating obstructive sleep apnea, including at least one implantable, tissue supporting filamentary element, and an insertion device including an outer tubular element having a tissue penetrating distal end and a side opening therein positioned proximal of the tissue penetrating distal end, and a grasping device movable between a first, retracted position wherein it is positioned entirely within an interior of the outer tubular element, and a second, extended position wherein the grasping device extends outwardly from the outer tubular element through the side opening therein. The grasper device is further is movable between open and closed positions such that the grasper device is adapted to grasp the filamentary element when in the closed position.

The filamentary element may be made of expanded polytetrafluoroethylene (ePTFE).

In another embodiment, the grasper device further includes first and second opposing hook elements, which may be opposing hooks that have a twisted configuration relative to one another, and which may further be made of nitinol.

In yet another embodiment, the tubular shaft of the insertion device further includes a visible indicator near the distal end thereof.

Also provided is a method for treating sleep conditions in a patient including implanting a biocompatible filamentary element across and within the submucosa of the patient's tongue such that first and second ends thereof extend outwardly from first and second puncture locations, passing a distal end of an insertion device having a grasping device positioned therein through a first pathway from a submental region of the patient, through the patient's genioglossus muscle and out of the tongue at a location proximal to the first puncture location, grasping the filamentary element with the grasping device at a location beneath the surface of the tongue and in proximity to the first puncture location, and withdrawing the insertion device and grasped filamentary element through said first pathway. The method further includes passing the distal end of the insertion device through a second pathway from a submental region of the patient, through the patient's genioglossus muscle and out of the tongue at a location proximal to the second puncture location, grasping the filamentary element with the grasping device at a location beneath the surface of the tongue and in proximity to the second puncture location, and withdrawing the insertion device and grasped filamentary element through the second pathway.

In one embodiment, the grasping steps further include deploying the grasping device through a side aperture of the insertion device, and the withdrawing steps further include at least partially retracting the grasping device to within the insertion device.

The grasper device may further include first and second opposing hook elements, which may further have a twisted configuration relative to one another, and may further be made of nitinol.

These and other objects, features and advantages of the present invention will be apparent from the following detailed description of illustrative embodiments thereof, which is to be read in connection with the accompanying drawings.

BRIEF DESCRIPTION OF THE DRAWINGS

FIGS. 1-3 illustrate the human anatomy;

FIG. 4 is a perspective view of an insertion device according to the present invention with grasping elements in a retracted position;

DETAILED DESCRIPTION

Figure 1:
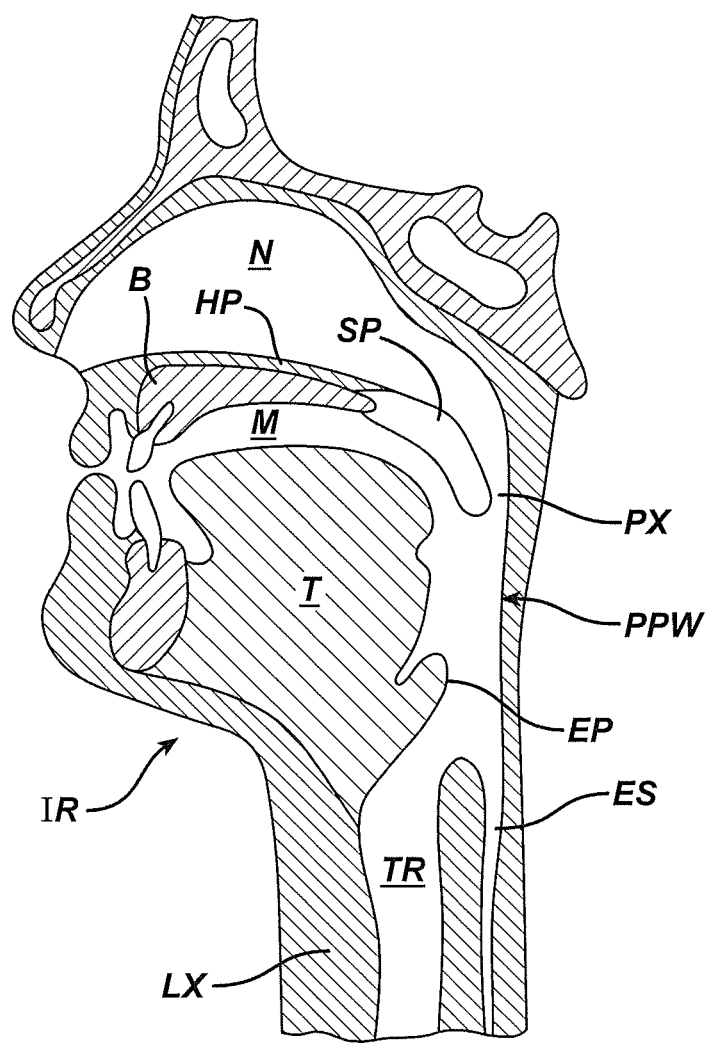

FIG. 1 shows a cross-section of a human head with anatomical structures including the nasal cavity N, bone B of the hard palate HP, the soft palate SP, the mouth M, the tongue T, the trachea TR, the epiglottis EP, the esophagus ES, and the posterior pharyngeal wall PPW. In the human head, an air filled space between the nasal cavity N and the larynx LX is referred to as the upper airway.

The most critical part of the upper airway associated with sleep disorders is the pharynx PX. Referring to FIG. 2, the pharynx has three different anatomical levels. The nasopharynx NP is the upper portion of the pharynx located in the back of the nasal cavity N. The oropharynx OP is the intermediate portion of the pharynx containing the soft palate SP, the epiglottis EP, and the curve at the back of the tongue T. The hypopharynx HP is the lower portion of the pharynx located below the soft tissue of the oropharynx OP. The oropharynx OP is the section of the pharynx that is most likely to collapse due to the high prevalence of soft tissue structure, which leaves less space for airflow. The hypopharynx HP lies below the aperture of the larynx and behind the larynx, and extends to the esophagus.

As is well known to those skilled in the art, the soft palate and the tongue are both flexible structures. The soft palate SP provides a barrier between the nasal cavity N and the mouth M. In many instances, the soft palate SP is longer than necessary and extends a significant distance between the back of the tongue T and the posterior pharyngeal wall PPW.

Although the muscles relax throughout the body during sleep, most of the muscles of the respiratory system remain active. During inhalation, the diaphragm contracts and causes negative pressure to draw air A into the nasal cavity N and the mouth M. The air then flows past the pharynx PX, through the trachea TR and into the lungs. The negative pressure causes the tissue of the upper airway to deform slightly, which narrows the airway passage. In apneic patients, the soft palate SP, the tongue T, and/or the epiglottis EP collapse against the posterior pharyngeal wall PPW to block airflow into the trachea. As the airway narrows, airflow through the pharynx becomes turbulent which causes the soft palate SP to vibrate, generating a sound commonly known as snoring.

During sleep, humans typically experience brief obstructions of airflow and/or small decreases in the amount of airflow into the trachea and lungs. An obstruction of airflow for more than ten seconds is referred to as apnea. A decrease in airflow by more than fifty percent is referred to as hypopnea. The severity of sleep disorders is measured by the number of apneas and hypopneas that occur during every hour of sleep.

If apnea or hypopnea occurs more than five times per hour, most medical personnel diagnose the individual as having an upper airway resistance problem. Many of these patients often exhibit symptoms related to sleep disorders including sleepiness during the day, depression, and difficulty concentrating. Individuals having ten or more episodes of apnea or hypopnea during every hour of sleep are officially classified as having obstructive sleep apnea syndrome. As the airway is obstructed, the individual makes repeated attempts to force inhalation. Many of these episodes are silent and are characterized by movements of the abdomen and chest wall as the individual strains to draw air into the lungs. Typically, episodes of apnea may last a minute or more. During this time, oxygen levels in the blood will decrease. Ultimately, the obstruction may be overcome by the individual generating a loud snore or awakening with a choking feeling.

Referring to FIG. 2, when an individual is awake, the back of the tongue T and the soft palate SP maintain their shape and tone due to their respective internal muscles. As a result, the airway A through the pharynx remains open and unobstructed. During sleep, however, the muscle tone decreases and the posterior surface of the tongue and the soft palate become more flexible and distensible.

Referring to FIG. 3, without normal muscle tone to keep their shape and to keep them in place either alone or as a group, the posterior surface of the tongue T, the epiglottis EP, and the soft palate SP tend to easily collapse to block the airway A.

The present invention provides an improved insertion device and method of use for tongue suspension procedures for treating obstructive sleep apnea or for other procedures involving the passage of a fiber or filamentary element in more than one direction through tissue that is to be suspended or supported through the use of a single puncture installation technique.

The insertion device 100 of the present invention is illustrated in FIG. 4, and includes a tapered tip 102 at a distal end 104 to enable dissection/tunneling through tissue, such as the fibrous muscular structures of the tongue, and an enlarged, first graspable element 103 near the proximal end 105 of any suitable size and configuration to enable a surgeon to grasp the insertion device. The first graspable element 103 is preferably formed with a raised feature 130 or projection to provide a non-symmetrical shape to faciliatate orientation of the device. The insertion device 100 includes a hollow outer tubular element 106 having the tapered tip 102 and a side aperture or opening 108 therein toward the distal end. In a preferred embodiment, the side opening 108 is positioned at a location approximately 1.5 cm from the distal end 104.

In the embodiment described, the raised feature 130 is located in a plane, illustrated as the x-y plane in FIG. 4, that passes through the midline axis of the device and passes perpendicular to the side opening 108. This orientation ensures that the raised feature is located directly opposite the side of the device with the side opening. Additionally, located at the proximal end 105 of the device there are two additional movable graspable elements. The second graspable element 126 is coupled with a mechanism for moving an inner, hollow tubular element 124 within the outer tubular element 106 (see FIG. 7), and is coupled with hook elements 116a and 116b that will be described further below. The third graspable element 122 is attached to a concentric central shaft 132 contained within the inner tubular element 124 and is in communication with the rod guide element 300 as will be described further below with reference to FIG. 8.

Figure 7:
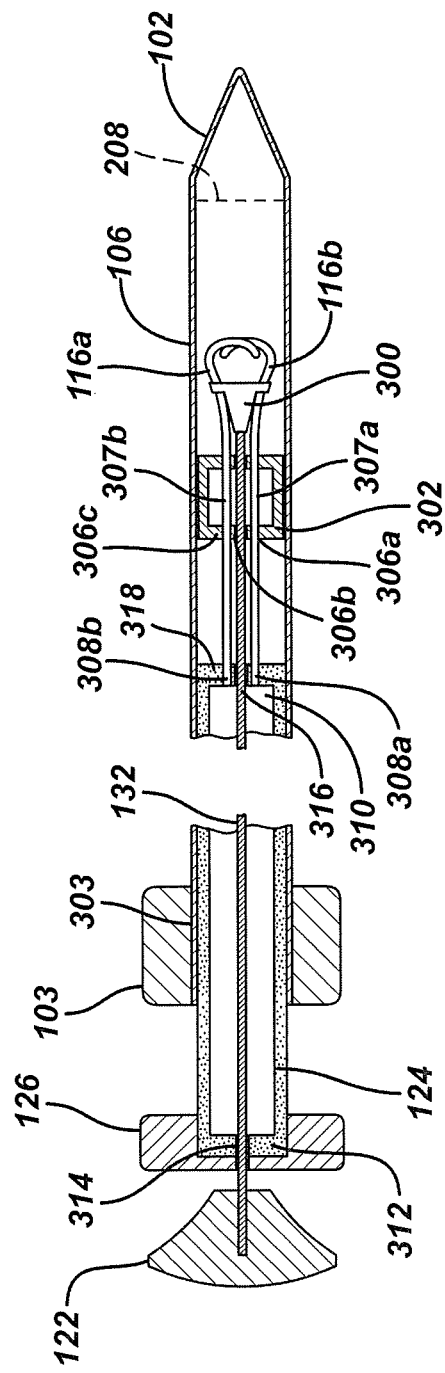
FIG. 7 is a cross-sectional, side view of the device of FIG. 4.

Referring now to FIG. 7, the components of the insertion device will be described in more detail. As indicated previously, the outer tubular element 106 includes a blunt tapered distal end or tip 102. This feature may be formed as a separate component that may be inserted into the open end of the outer tubular element. An alternative version may involve the attachment of a tapered tip component through the use of any suitable bonding means, such as welding, adhesives, threaded fittings, insert fitted components or other mechanical means. Alternatively, the distal tip of the outer tubular element may be formed into a blunt tip and exposed seams fused or sealed. A guide bearing component 302 is located within the outer tubular element 106. The guide bearing includes three passages 306a, 306b, and 306c, all of which are sized to enable free motion of the shaft portions 307a, 307b of the two hook elements 116a and 116b and the central shaft element 132 within the passages. The hook shaft portions of the elements 116a and 116b and the central shaft element 132 are installed within the hollow outer tubular element 106 and are passed through the guide passages 306a, 306b and 306c in the guide bearing 302. The proximal end 303 of the outer tubular element is fixed to the first graspable element 103.

The inner tubular element 124 is formed with closed ends 310 and 312. The closed ends may be formed as separate components that may be inserted into the open ends of the inner tubular. Alternative versions may involve the attachment of ends through the use of any suitable bonding means, such as welding, adhesives, threaded fittings, insert fitted components or other mechanical means, or forming the ends into a closed tip with exposed seams fused or sealed. The closed ends of the inner tubular element 124 are produced with central openings 314 and 316. These two openings are sized to allow sufficient clearance to pass the center shaft element 132 freely through the length of the inner tubular element. Proximal ends 308a, 308b of the shaft portions of the hook elements are attached to the distal end 318 of the inner tubular element. In the illustrated embodiment, the distal end 318 of the inner tubular element is produced with two additional openings that are sized to receive the proximal ends 308a, 308b of the shafts of the hook elements 116a and 116b. The free ends of the hook elements are bonded to the distal end through the use of press fits, welding, adhesives, threaded connectors, or other suitable means so that the inner tubular element 124 is fixedly coupled to the second graspable element 126. The proximal end of the central shaft 132 is fixedly coupled to the third graspable element 122.

The shaft and tubular elements (132, 106, 124) are movable relative to each other in an axial direction. The inner tubular element 124 may be moved in an axial manner within the inner lumen of the outer tubular element 106. To advance the inner tubular element, the first graspable element 103 is held in a fixed position. The second graspable element 126 is then manipulated towards or away from the first graspable element 103 to slide the inner tubular element within the lumen of the outer tubular element. The central shaft is able to be moved relative to the inner tubular element or relative to the outer tubular element. In order to advance the central shaft, either or both of the first 103 or second 126 graspable elements are held in a fixed position and the third graspable element 122 is either advanced towards or away from the first two graspable elements.

Figure 8A:
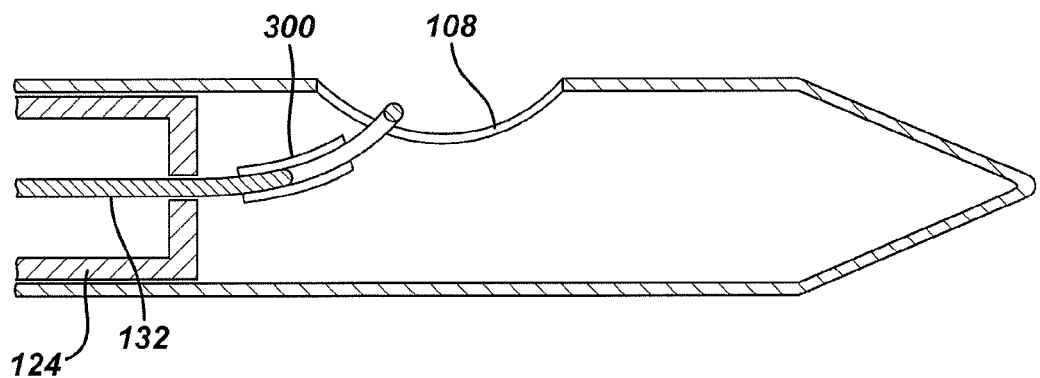
FIGS. 8a and 8b are enlarged, cross-sectional views of the distal end of the device of FIG. 4 along the x-z and x-y planes of FIG. 4 respectively.
Figure 8B:
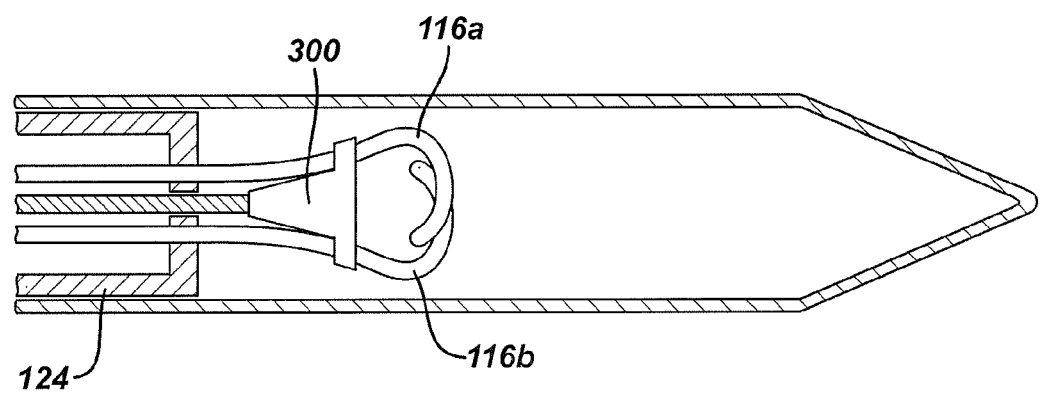

FIG. 8 illustrates cross-sectional views (in the x-z plane and x-y plane respectively of FIG. 4) of the distal end region of the insertion device with the hook like elements 116a, 116b in a retracted position. The shafts 307a, 307b of the hook like elements are seated within the respective guide bearing passages along with the distal end of the central shaft.

Figure 5:
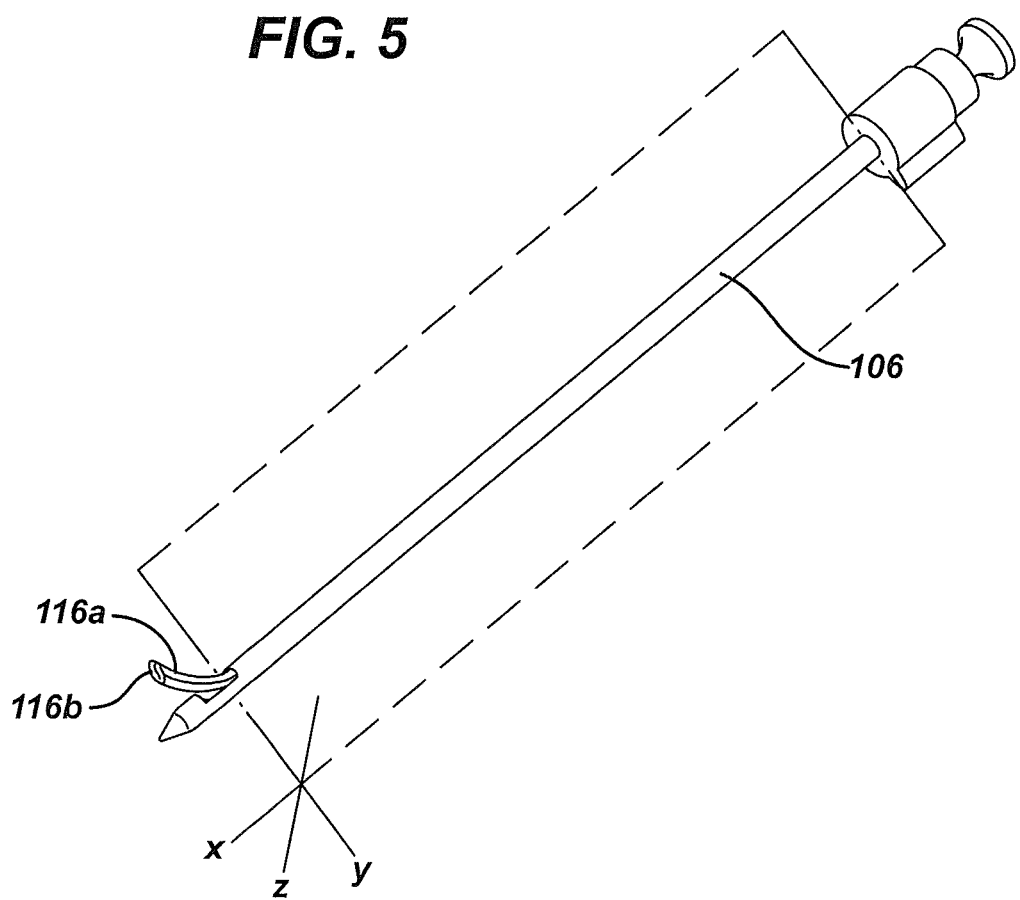
FIG. 5 illustrates the device of FIG. 4 with grasping elements in an extended, closed position.
Figure 6:
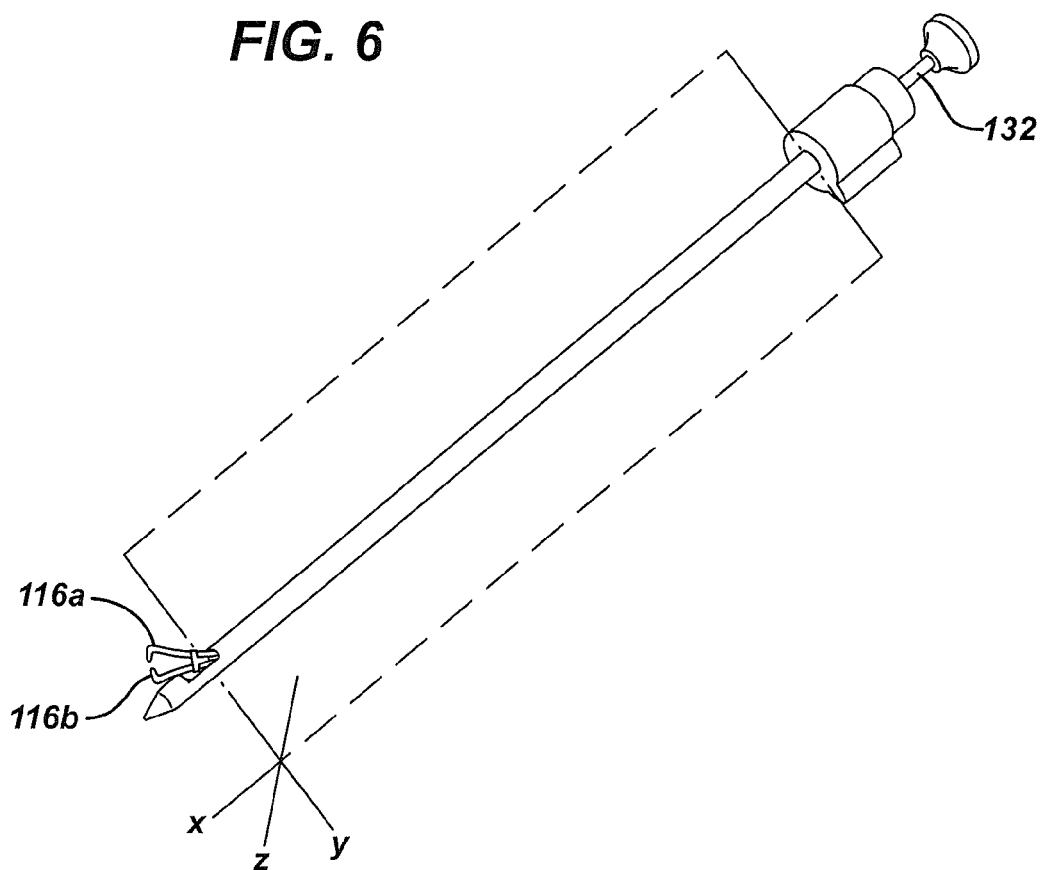
FIG. 6 illustrates the device of FIG. 5 with the grasping elements in an extended, open position.
Figure 9A:
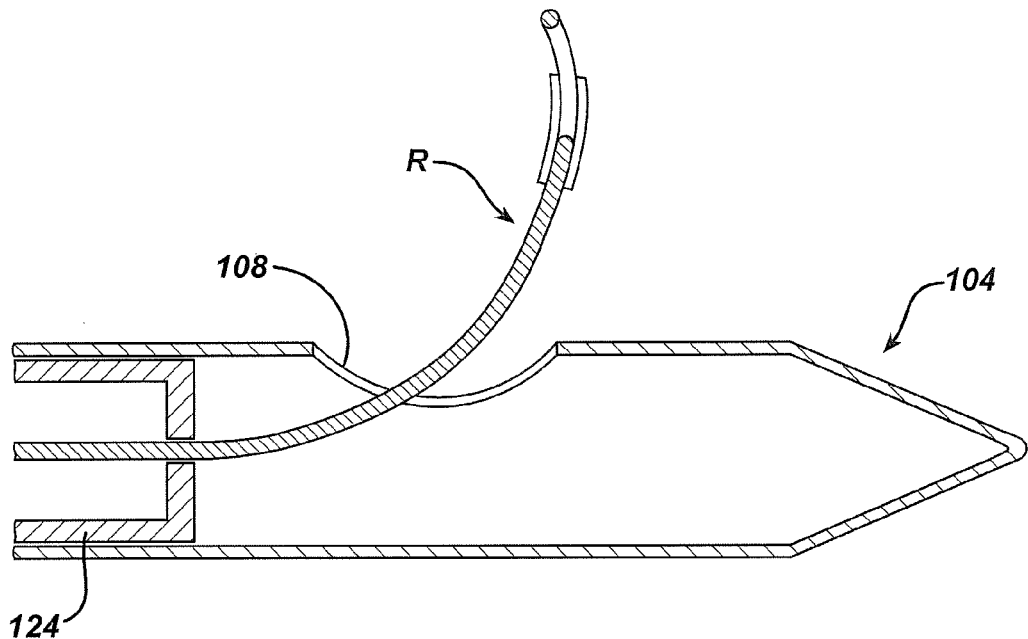
FIGS. 9a and 9b are enlarged, cross-sectional views of the distal end of the device of FIG. 5 along the x-z and x-y planes of FIG. 5 respectively.
Figure 9B:
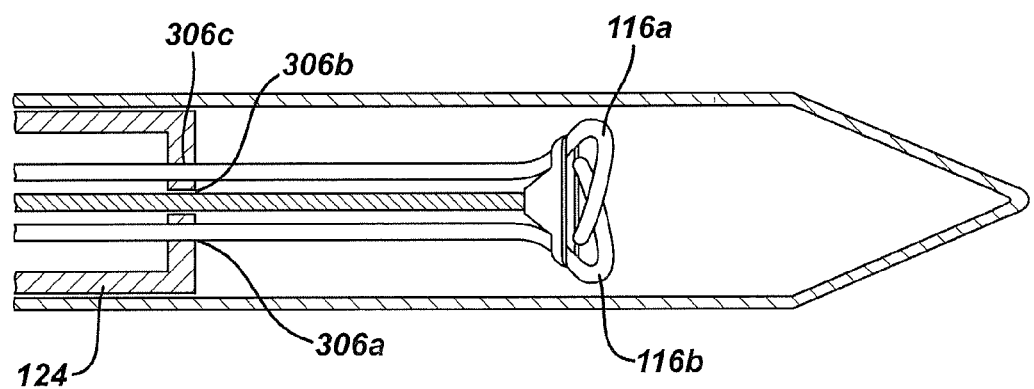
Figure 19A:
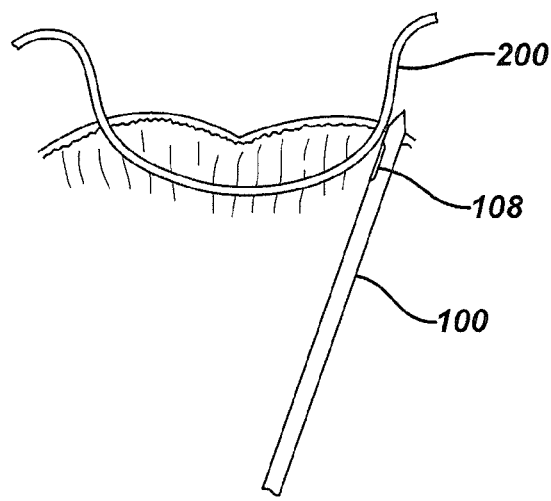
FIGS. 19a-19c further illustrate placement of a filamentary implant within the tongue using the insertion device of the present invention.
Figure 19B:
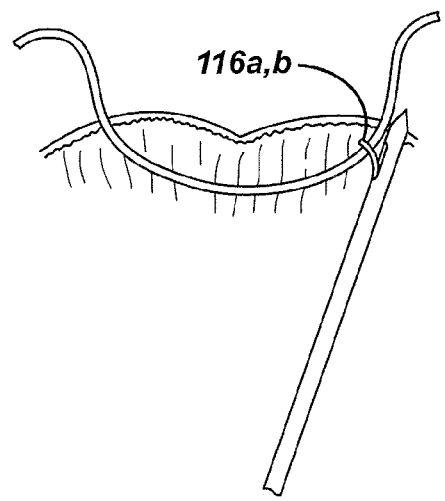
Figure 19C:
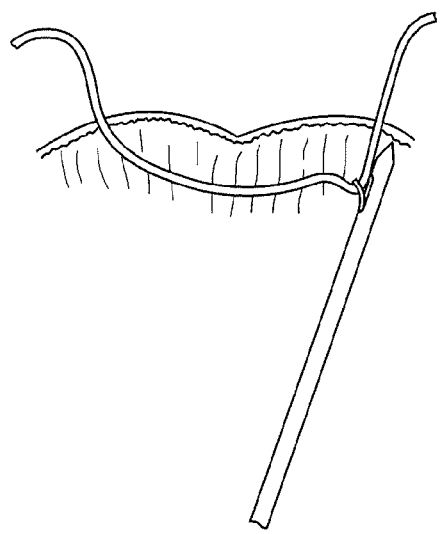

FIG. 9 illustrates cross-sectional views (in the x-z plane and x-y plane respectively of FIG. 5) of the distal end region of the insertion device with the hook like elements in an extended or ejected position. In order to eject the hook like elements from the side aperature 108 of the device, the central shaft 132 and inner tubular element 124 are axially advanced towards the distal end 104 of the insertion device while the first graspable element 103 is held in a fixed position. As these two members are advanced, the hook like elements 116a and 116b and central shaft 132 are advanced through the guide bearing passages 306a, 306b and 306c. In the preferred embodiment, the hook like elements are produced with a bend radius R such that when advanced and free from the constraint of the rod guide element 300 the elements form an arced geometry. The distal end of the central shaft is similarly formed with a bend radius that is similar to the radius of the hook like elements. The hook like elements may be formed from materials capable of providing a spring like deflections such as steel, stainless steel, brass, nitinol, etc. and polymeric materials such that the hook elements may be withdrawn into the guide bearing component and may be forcibly deformed into an essentially straight geometry and may be subsequently ejected through the side opening 108 in the outer tubular element 106 to resume a curved geometry. Upon forcible ejection, the hook like elements move from a retracted position where both reside fully within the outer tubular element, to an extended position wherein a tunnel is formed through the musculature of the tongue along a curved deployment path as illustrated in FIGS. 19a-19c and described further below.

Figure 10A:
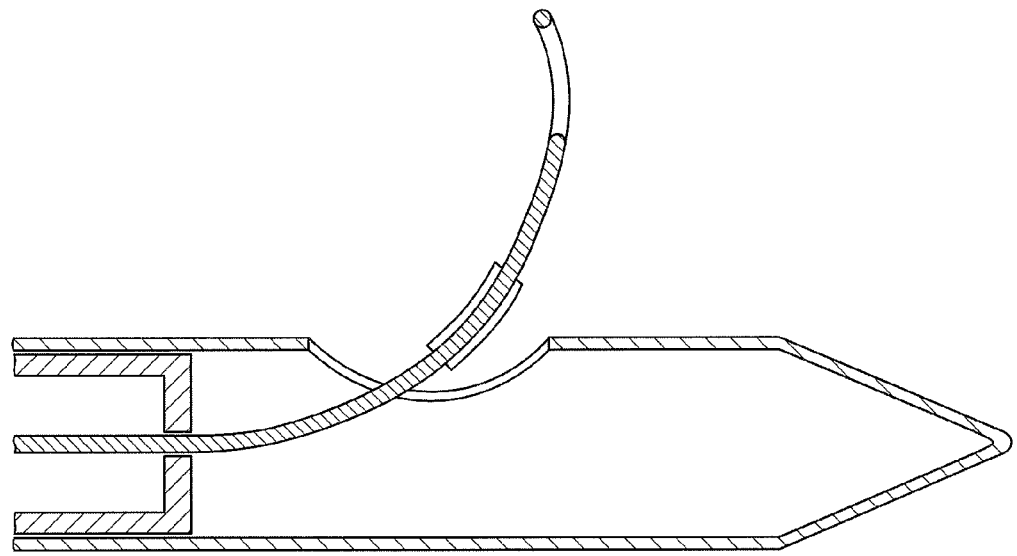
FIGS. 10a and 10b are enlarged, cross-sectional views of the distal end of the device of FIG. 6 along the x-z and x-y planes of FIG. 6 respectively.
Figure 10B:
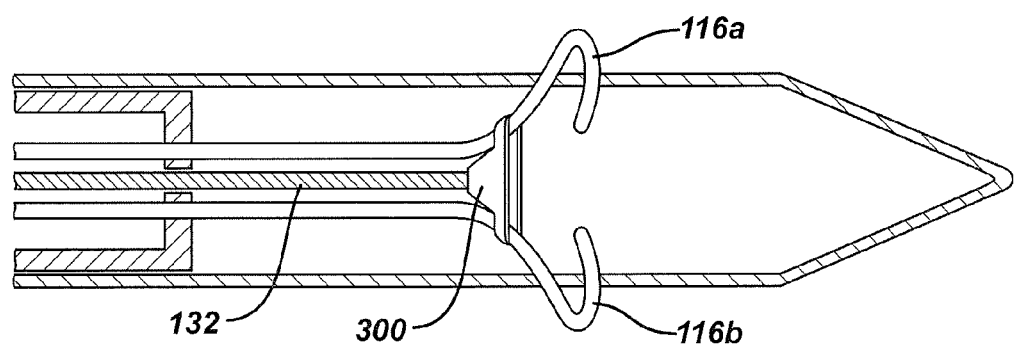

FIG. 10 illustrates cross-sectional views of the distal tip after the hook like elements 116a and 116b have been forcibly separated when in the ejected or extended position. In order to open the hook like elements, the first and second graspable elements 103 and 126 are held in fixed proximity relative to each other. The third graspable element 122 is withdrawn proximally to force the rod guide element 300 proximally relative to the fixed position of the hook like elements. The rod guide element is formed with two converging passages which provide control of the hook like element shafts. The converging passages of the rod guide element serve as a wedge like feature relative to the hook like elements' shafts 307a, 307b. As the wedge like feature is moved in a proximal direction, the shafts of the hook like elements are forced in opposite directions. While the rod guide element is illustrated as a simple angular wedge, arcuate passages are envisioned whereby the forcible motion of the rod guide may provide greater spreading deflection of the hook like elements. Additionally, the use of the arcuate passages may also enable plastic deformation of hook like element shafts to compensate for the use of materials in the hook like element shafts that demonstrate low spring rate. Once the hook like elements have been advanced and separated through motion relative to the guide bearing and the rod guide, the hooked ends of the elements open in a position that is lateral and distal to the opening 108 in the side of the to the insertion device 100 as shown in FIG. 10. As the hook like elements are advanced and opened, an implant such as a filamentary implant 200 (to be described further with reference to FIGS. 11-17) may be positioned within the hook like elements and may then be captured though the reverse motions of the rod guide element and the shafts through the bearing passages. As the distal tips of the hook elements bypass each other in an opposing fashion as shown in FIG. 8, the filamentary implant 200 is captured therebetween and may be withdrawn through tissue (see FIGS. 19a-c) as the bypassing hooks act as an eyelet or snare like feature on the insertion device.

Figure 11:
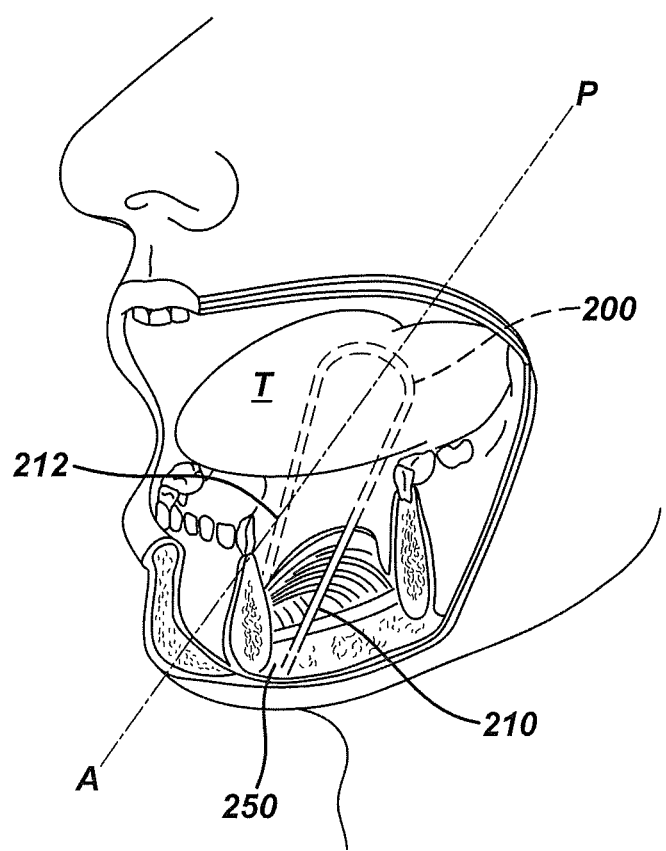
FIGS. 11-18 illustrate various steps for using an insertion device of the present invention to insert an implant for treating obstructive sleep apnea.

A method for using the insertion device will now be described in detail with reference to FIGS. 11-19. As indicated previously, the devices described herein have particular application for tongue suspension for the treatment of OSA. FIG. 11 illustrates a fiber-like or filamentary element 200 implanted within the tongue T. The leading and trailing legs of the filamentary element 210, 212 preferably extend toward to a location that is within the posterior aspect of the mental tubercle, near the genio hyoid tubercle and are anchored at substantially a common fixation point 250. The filamentary element may be either fixed to the soft tissues directly or through the use of a soft tissue anchor mounted inferior to the mylohyoid muscle, or may be anchored directly to the mandible, slightly inferior to the genio hyoid tubercle either directly or through the use of common bone anchor technologies such as screws, wedges, posts, and other such means.

Figure 12:
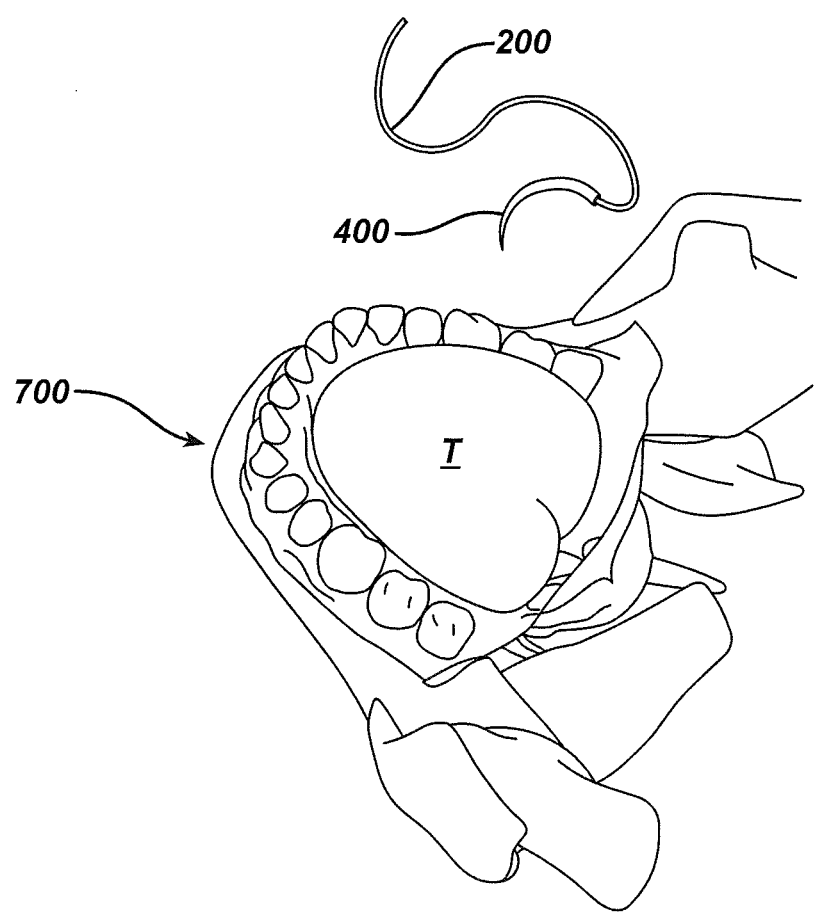
Figure 13:
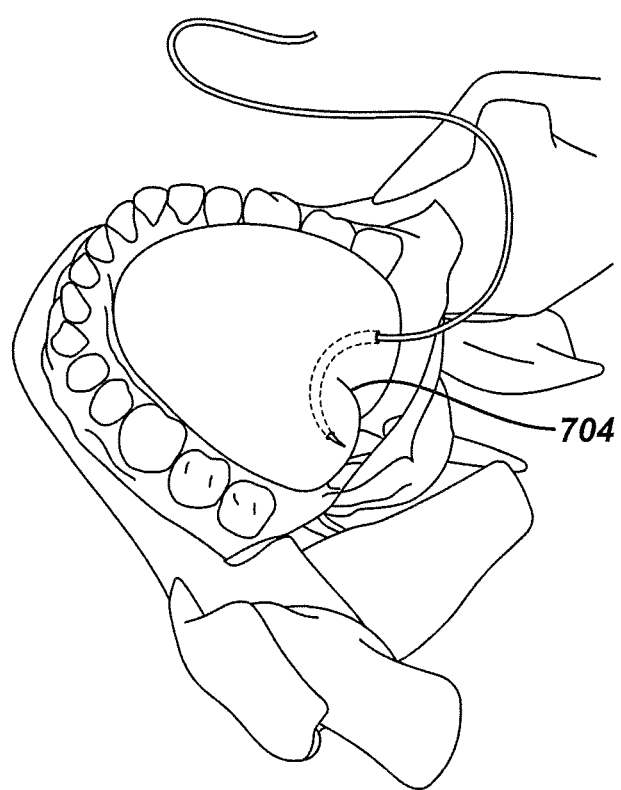
Figure 14:
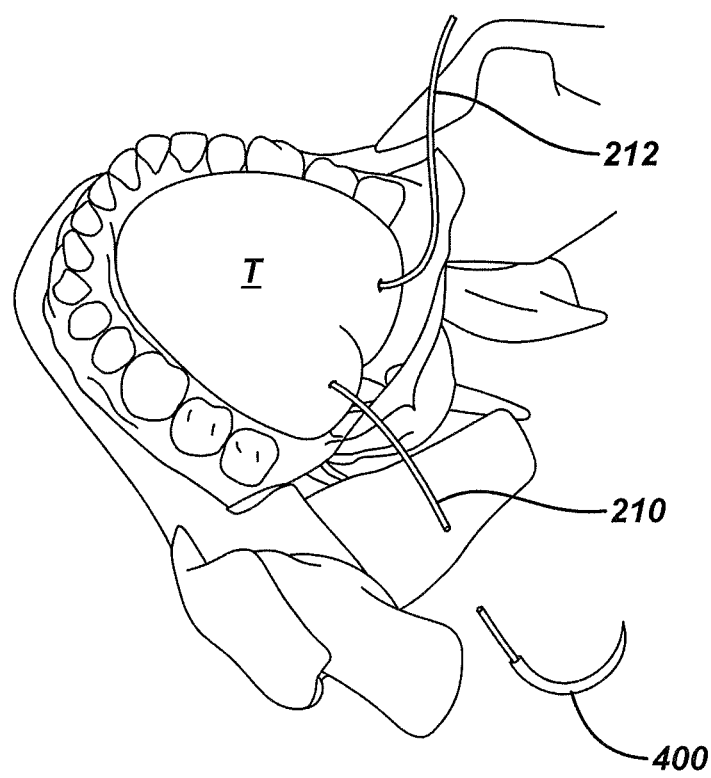
Figure 15:
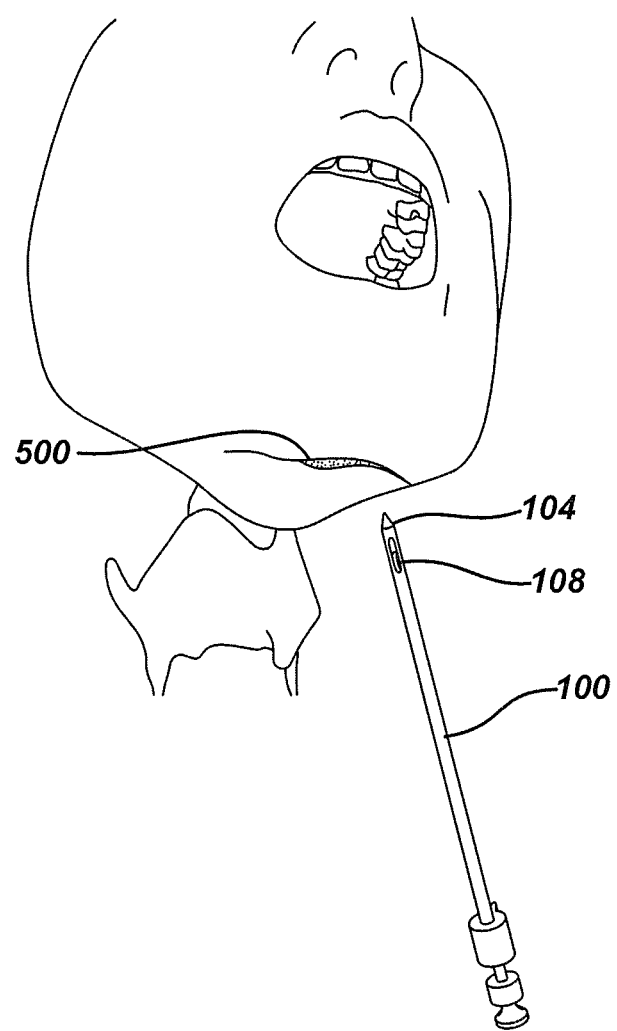
Figure 16:
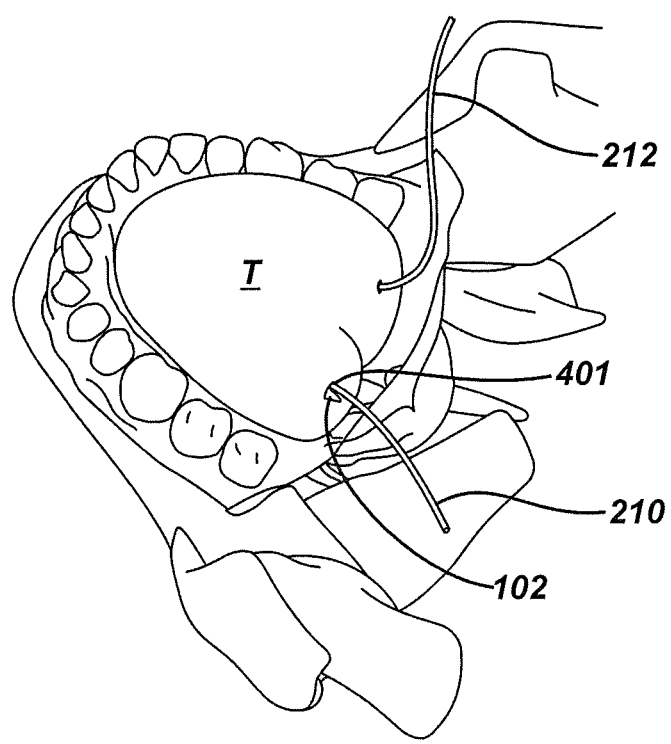
Figure 17:
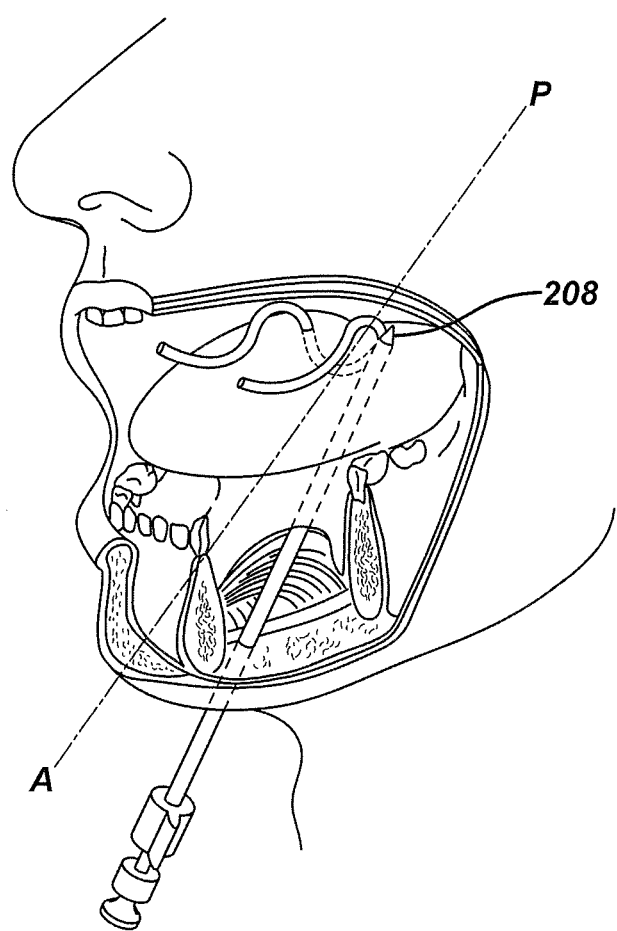
Figure 18:
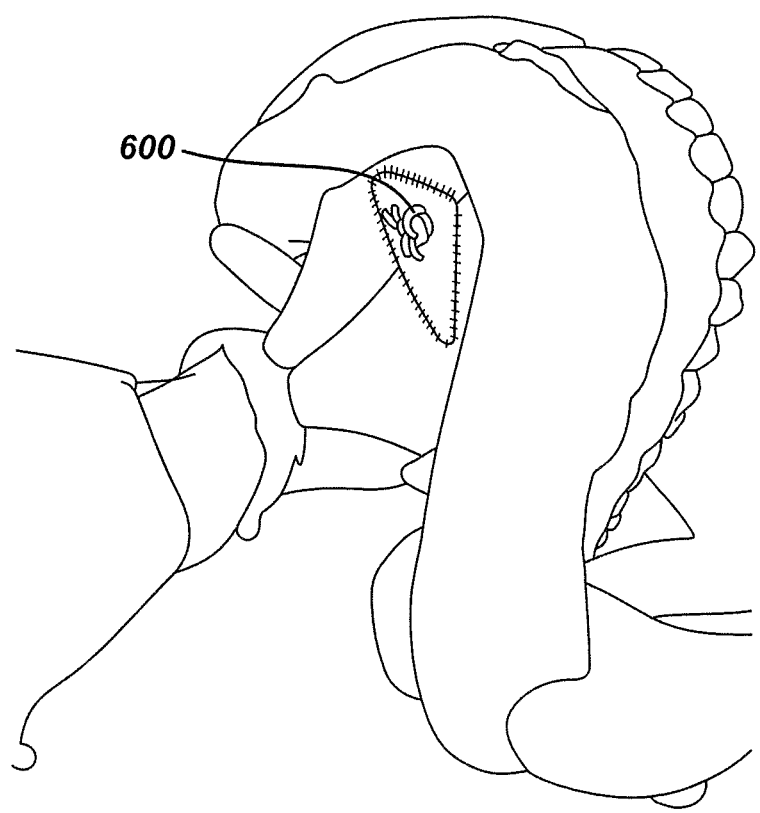

Referring now to FIGS. 12-19, the installation of the filamentary element into the tongue with a common fixation point will be described in detail. FIG. 12 provides an illustration of the human mandible 700 in a simplified form to enable clear visualization of the tongue T. The filamentary element 200 with the needle 400 attached is provided for passage through the tongue T. Referring to FIG. 13, it can be seen that the needle is passed in a lateral direction with the punctures placed approximately one centimeter from the midline 704 of the tongue. Referring next to FIG. 14, the needle is passed entirely through the tongue until the central region of the fiber is located within the tissues of the tongue. The needle 400 is then removed either by cutting the filamentary element or removing any other mechanical connection means that may be employed. As can be seen in FIG. 15, a lateral sub-mental incision 500 is made to expose the musculature. The insertion device 100 is then utilized to create a pathway for the fiber to the pass through the tongue from the inferior incision, through the mylohyoid and genioglossus muscles and exiting through the mucosal surface of the tongue within the oral cavity. The insertion device is advanced through the tongue from the sub-mental region to create a tunnel through the tissue. The distal tip of the insertion device is guided to the puncture site 401 previously created by the needle 400 in the lateral portion of the tongue mucosal surface. Referring to FIGS. 16 and 17, the tapered tip 102 of the insertion device is inserted through the mucosal tissue of the tongue in the oral cavity, and positioned with the base of the tapered tip at the level of the mucosal tissues. The tapered tip and insertion device is positioned lateral to the filamentary element exiting the tongue. The insertion device 100 is advanced until a marking 208 on the external shaft 106 is visible outside of the tongue, or a similar measure is observed such as extension of the external shaft from the surface of the tongue by a predetermined distance. This observed measure will further indicate that the side opening 108 of the external shaft 106 is positioned a certain distance beneath the surface of the tongue. Further, any suitable marker may be present on the insertion device to indicate to the surgeon the directional location of the side opening relative to the implanted filamentary element. The insertion device is then rotated about its central axis until the raised element 130 on the first graspable element 103 is positioned opposite the position of the filamentary element within the tongue. This positioning ensures that the hook elements will engage with the filamentary element within the tissues of the genioglossus upon ejection from the side opening 108 of the insertion device. The hook elements 116a, 116b are ejected from the aperture as previously described and are opened to engage with the filamentary element as shown in FIGS. 19a-19b. It can be seen that as the hook elements are advanced out of the side opening 108 of the insertion device, the hooks pass by the filamentary element 200 laterally from the instrument, or towards the midline of the genioglossus. The hook elements are then closed about the filamentary element through the retraction of the rod guide shaft. This motion causes the two hook elements to form essentially a snare about the filamentary element. The closed hook elements are then retracted into the aperture of the insertion device as previously described. The closed hook elements close loosely about the filamentary element and allow for slippage of the filamentary element within the hooks. As the filamentary element is retracted towards the insertion device, it is pulled into the genioglossus through the natural arced tunnel formed by the needle 400 and into the path created by the hook elements 166a and 116b and is thereby redirected away from the puncture located in the mucosal surface of the tongue. This redirection of the fiber prevents the formation of a crease or fold location in the fiber under the mucosal puncture. Since the fiber path has been altered, there is a minimization of the potential for the mucosal puncture to be propped open by the folded fiber. Once the hooks elements are fully seated within the insertion device 100, the device is withdrawn from the tissues from the submental incision and the free end 210 of the filamentary element is released from the insertion device. The insertion device is then re-inserted into the genioglossus to redirect and retrieve the second free end 212 of the filamentary element. Tension is applied to the free ends of the fiber to advance the tongue base as is necessary and the free ends of the fiber are either tied in a knot 600, clipped or clamped to the fixation anchor as illustrated in FIG. 18.

Figure 20A:
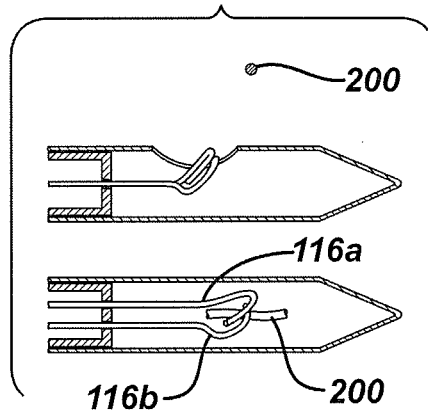
FIGS. 20a-20d are enlarged views of the distal end of an exemplary insertion device according to the present invention grasping a filamentary implant.
Figure 20B:
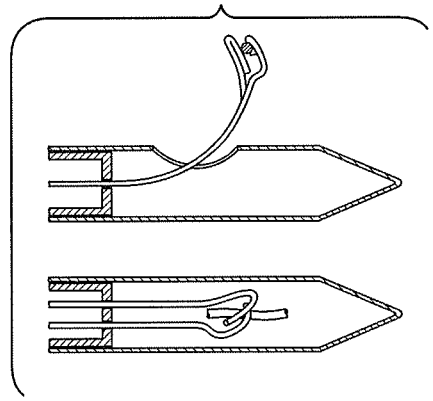
Figure 20C:
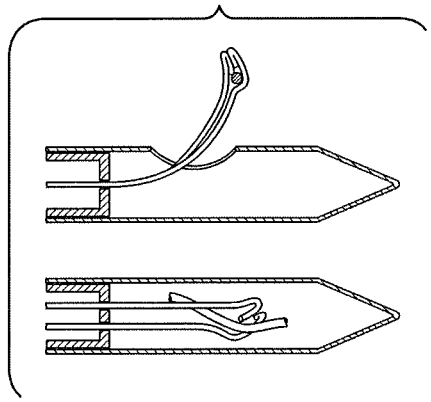
Figure 20D:
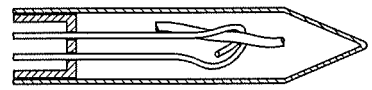
Figure 21A:
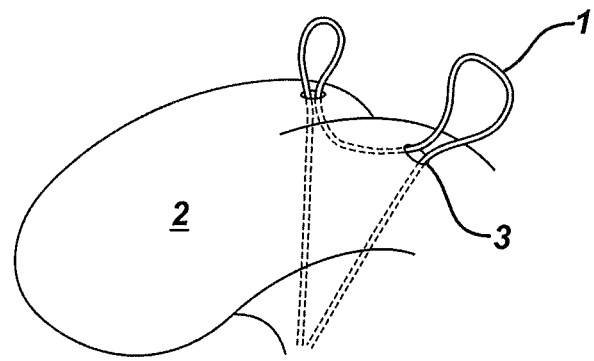
FIGS. 21a and 21b illustrate a typical prior art placement of a tongue suspension loop.
Figure 21B:
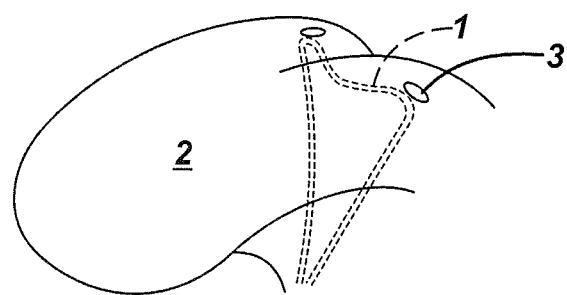

As was noted previously, the hooks 116a, 116b of the grasper device are preferably located side by side, but may also have a twisted geometry to facilitate passive snaring of the filamentary element as shown in FIG. 20a. In this manner, as the hooks are advanced past the filamentary element as shown in FIGS. 20b and 20c, the angled or twisted geometry facilitates spreading of the hooks and passage over the filamentary element. Once the distal ends of the hook elements pass the filamentary element, they collapse inward towards each other to trap or snare the filamentary element therebetween as shown in FIG. 20c. Once the hook elements have snared the filamentary element, they are withdrawn into the outer tubular element 106, as shown in FIG. 20d, which draws the filamentary element down from the previously lateral path as shown in FIG. 21, through the new path created by the insertion device.

Although illustrative embodiments of the present invention have been described herein with reference to the accompanying drawings, it is to be understood that the invention is not limited to those precise embodiments and that various other changes and modifications may be effected herein by one skilled in the art without departing from the scope or spirit of the invention.

What is claimed is:

1. An insertion device comprising:
    an outer tubular element extending along a longitudinal axis and having a tissue penetrating distal end and a side opening therein positioned proximal of said tissue penetrating distal end;
    an inner tubular element extending along said longitudinal axis and positioned partially within an interior of said outer tubular member, and movable longitudinally relative to said outer tubular element;
    a grasping device fixedly coupled to the inner tubular element and extending outward in a distal direction from said inner tubular element; and
    a central shaft extending along said longitudinal axis and through an interior of said inner tubular element, and movable longitudinally relative to both the inner and outer tubular elements, a distal end of said central shaft being slidably coupled with said grasping device;
    wherein said inner tubular element is further movable between a retracted position wherein the grasping device is positioned entirely within the interior of the outer tubular element, and an extended position wherein the grasping device extends outwardly from the outer tubular element through said side opening, and
    wherein when the inner tubular element is in the extended position, the grasping device is movable between open and closed positions such that the grasping device is adapted to grasp a filamentary element positioned external of the outer tubular element and in proximity thereto.

2. The insertion device according to claim 1, wherein the grasper device further comprises first and second grasping elements.

3. The insertion device according to claim 2, wherein the first and second grasping elements are opposing hook-like elements.

4. The insertion device according to claim 3, wherein the first and second grasping elements are comprised of nitinol.

5. The insertion device according to claim 3, wherein the first and second hook-like elements are opposing hooks have a twisted configuration relative to one another.

6. The insertion device according to claim 1, further comprising a visible indicator near the distal end of the outer tubular element.

7. The insertion device according to claim 1, further comprising:
    a first grasping element fixedly coupled to said outer tubular element such that movement of the first grasping element by a user causes movement of the outer tubular element longitudinally relative to the inner tubular element and central shaft;
    a second graspable element fixedly coupled to the inner tubular element such that movement of the second graspable element by a user causes movement of the inner tubular element longitudinally relative to the outer tubular element and central shaft; and
    a third graspable element fixedly coupled to the central shaft such that movement of the third graspable element by a user causes movement of the central shaft longitudinally relative to the inner and outer tubular elements.

8. The device according to claim 7, wherein the central shaft passes longitudinally through said inner tubular element via first and second openings in first and second closed ends of the inner tubular element respectively.

9. The device according to claim 8, wherein the inner tubular element extends outwardly from an open proximal end of the outer tubular element.

10. A method for treating sleep conditions in a patient comprising:
    implanting a biocompatible filamentary element across and within the submucosa of the patient's tongue such that first and second ends thereof extend outwardly from first and second puncture locations;
    passing a distal end of an insertion device having a grasping device positioned therein through a first pathway from a submental region of the patient, through the patient's genioglossus muscle and out of the tongue at a location proximal to the first puncture location;

grasping the filamentary element with the grasping device at a location beneath the surface of the tongue and in proximity to the first puncture location;

withdrawing the insertion device and grasped filamentary element through said first pathway;

passing the distal end of the insertion device through a second pathway from a submental region of the patient, through the patient's genioglossus muscle and out of the tongue at a location proximal to the second puncture location;

grasping the filamentary element with the grasping device at a location beneath the surface of the tongue and in proximity to the second puncture location; and withdrawing the insertion device and grasped filamentary element through said second pathway.

11. The method according to claim 10, wherein the grasping steps further comprise deploying the grasping device through a side aperture of the insertion device; and the withdrawing steps further comprise at least partially retracting the grasping device to within the insertion device.

12. The method according to claim 10, wherein the grasper device of the inserter device further comprises first and second opposing hook elements.

13. The method according to claim 12, wherein the first and second opposing hooks have a twisted configuration relative to one another.

14. The method according to claim 12, wherein the first and second opposing hook elements are comprised of nitinol.

* * * * *